United States Patent [19]

Anis

[11] Patent Number: 4,908,015
[45] Date of Patent: Mar. 13, 1990

[54] CATARACT REMOVAL TECHNIQUE

[76] Inventor: Aziz Y. Anis, 9540 Firethorn La., Lincoln, Nebr. 68520

[21] Appl. No.: 224,579

[22] Filed: Jul. 26, 1988

[51] Int. Cl.<sup>4</sup> ............................................... A61B 17/00
[52] U.S. Cl. ....................................... 604/22; 604/28; 606/166
[58] Field of Search .................... 128/305, 303 R, 318, 128/751–754, 898; 604/28, 22, 51

[56] References Cited

U.S. PATENT DOCUMENTS

| | | | |
|---|---|---|---|
| 3,589,363 | 6/1971 | Banko | 604/22 |
| 3,937,222 | 2/1976 | Banko | 128/305 |
| 4,191,176 | 3/1980 | Spina et al. | 604/28 X |

*Primary Examiner*—Michael H. Thaler
*Attorney, Agent, or Firm*—Vincent L. Carney

[57] ABSTRACT

To remove a cataract, a cannula is inserted through a plurality of layers of compacted material in the lens and fluid of between 1/500 and 1/100 of a milliliter is injected to separate the layers of the lens cortex and lens nucleus. These steps are repeated until the nucleus and cortex of the lens are decompacted at increasing penetrations until a compacted portion of the nucleus is reached which resists the insertion of a needle. An elongated tool is inserted through an incision into the capsular chamber and against the lens to cut the lens in a series of paths diverging from the incision and thus to break the lens into a series of wedge-shaped sections. The tool may have an ultrasonic vibrator mounted within its center, whereby the cutting action is aided.

10 Claims, 4 Drawing Sheets

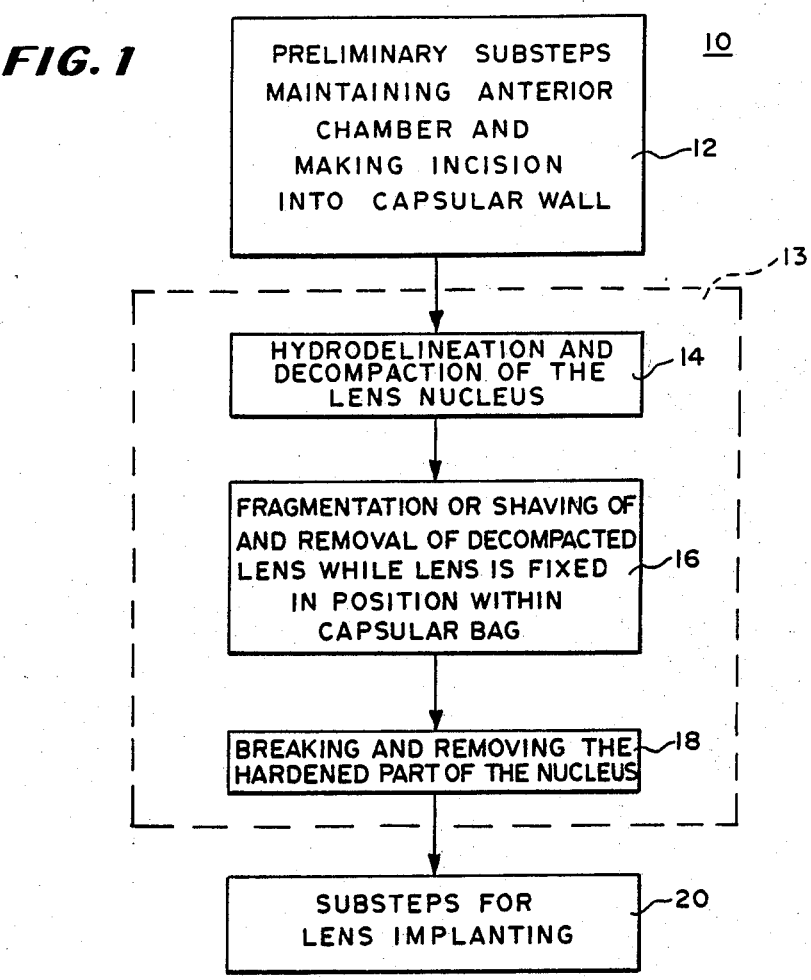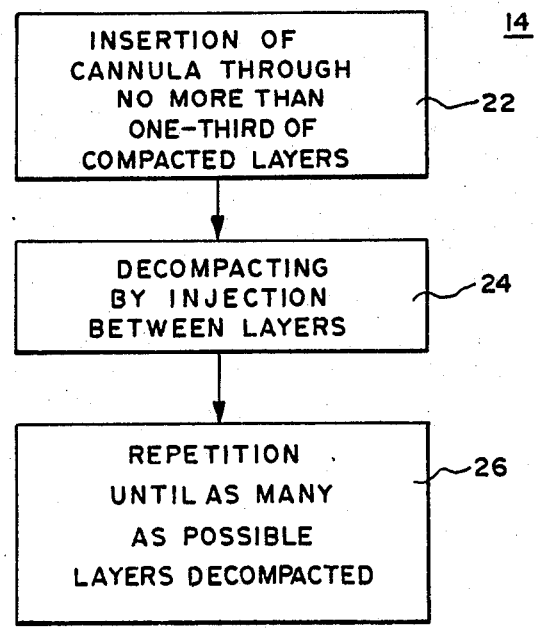

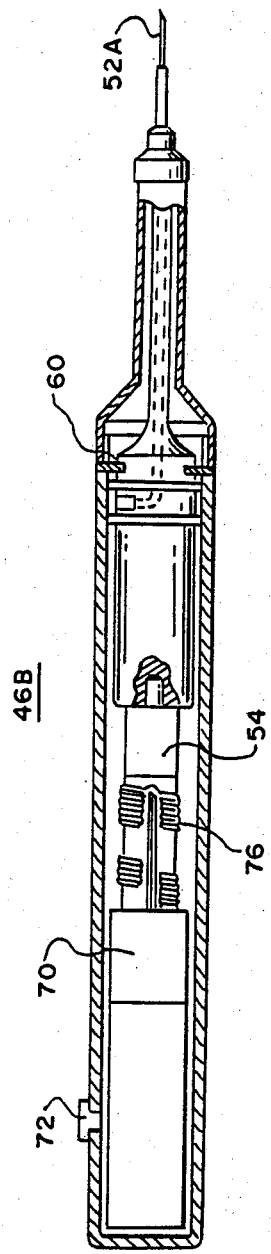
FIG. 10
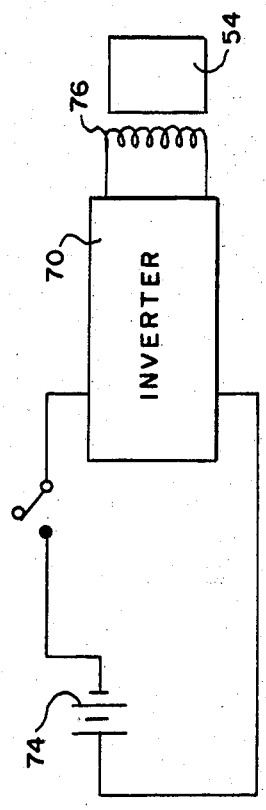
FIG. 11
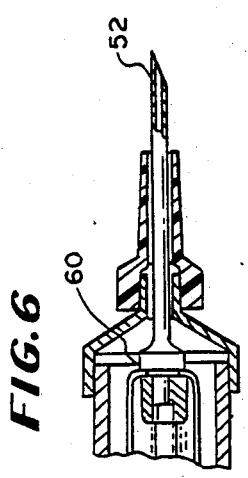
FIG. 6
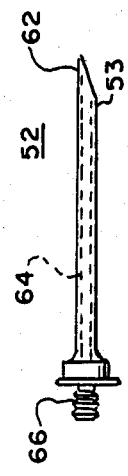
FIG. 7
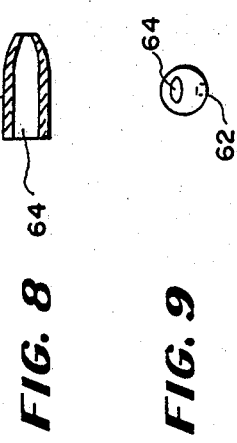
FIG. 8
FIG. 9

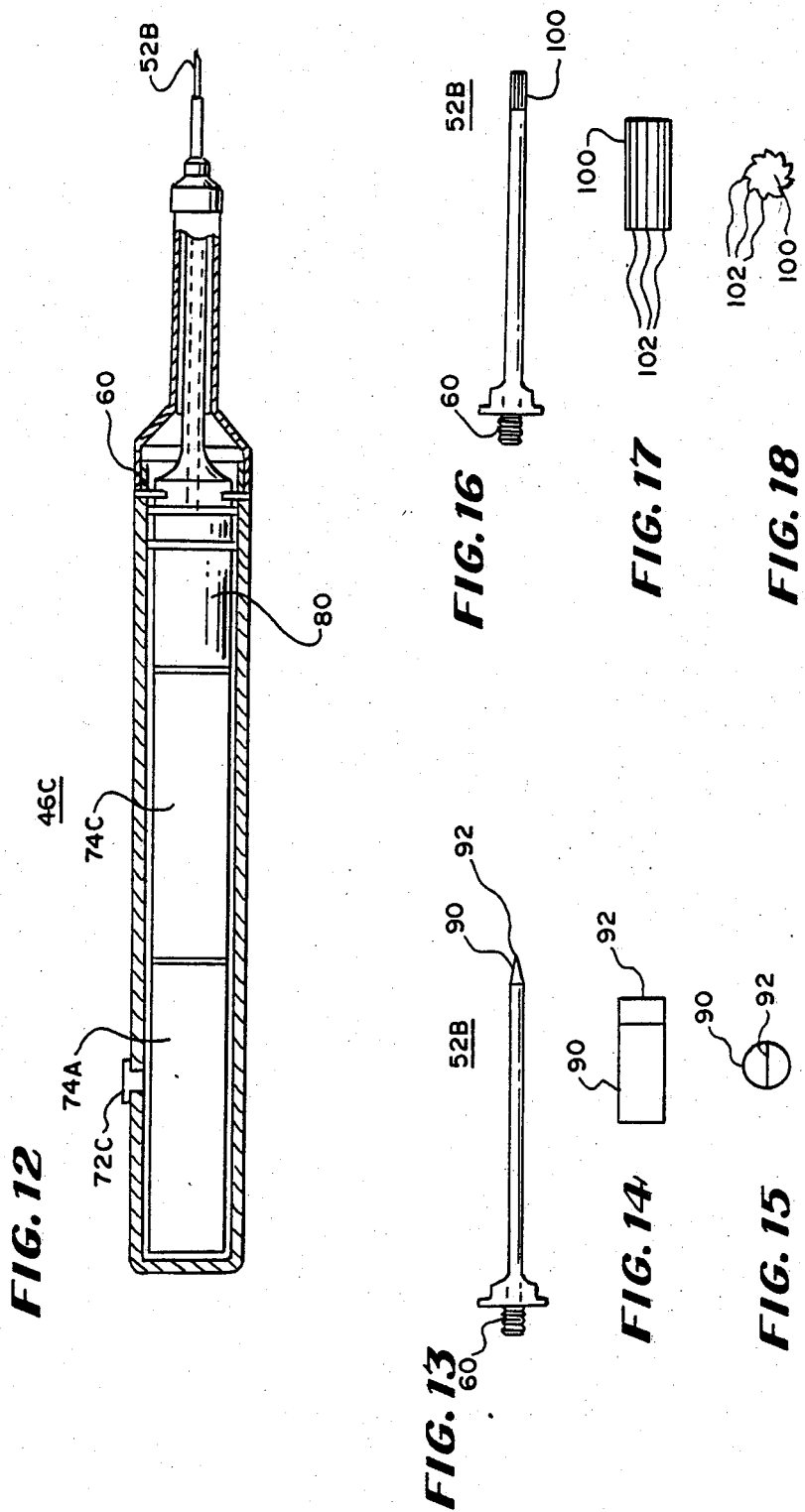

CATARACT REMOVAL TECHNIQUE

BACKGROUND OF THE INVENTION

This invention relates to the removal of cataracts and to equipment for such removal.

In one prior art surgical technique for the removal of cataracts: (1) an incision is made along the superior corneal margin from about 10 to 2 o'clock (12 o'clock is the location closest to the top of the head of the patient) approximately 10 mm in chord length; (2) a large part of the anterior capsule is removed; (3) the nucleus is expressed out of the eye; (4) the cortex is removed by a process of irrigation and aspiration; and (5) the lens is replaced with a lens implant. The anterior chamber is maintained substantially formed during the operation by means of a continuous inflow of irrigating solution in an amount ranging from 50 to 500 ml.

In one other prior art technique designed to improve the above in substantially reducing the amount of irrigating fluid to no more than 1-3 milliliters: (1) an incision is made along the superior margin of the cornea from 10 to 2 o'clock; (2) the anterior chamber is filled with viscoelastic compound to maintain its usual form; (3) a horizontal incision in the anterior capsular wall is made at a location away from the center of the capsular bag; (4) the nucleus is removed with a vectis; and (5) about 0.1 milliliter of liquid is introduced into the capsular bag to separate the capsular walls. A wedge of the cortex is engaged in the aspiration port of a cannula and peeled toward the center and then aspirated to remove it behind the anterior capsule within the capsular cavity. This process is repeated so that the layers of the cortex are peeled and then aspirated inwardly through the cannula layer by layer until the intact capsular bag (except for the horizontal incision) is completely empty and clean. This technique of removing the cataract is disclosed by Anis, Aziz Y. "Illustrated Step-by-Step Description of the Anis Dry Extra Capsular Cataract Extraction Technique With In-the-Bag Lens Implementation"; Seminars in Opthalmology, v. 1, N. 2 (Jun.), 1986, pp. 113-129.

This technique has the disadvantage of requiring a larger incision than desirable. Two prior art types of instruments which aid in the fragmentation and aspiration of the lens nucleus to permit extraction through a small incision are disclosed in U.S. Pat. No. 3,589,363 to Anton Banko, et al.; U.S. Pat. No. 3,902,495 to Steven N. Weiss; U.S. Pat. No. 3,693,613 to Charles Kelman, et al.; and U.S. Pat. No. 4,041,947 to Steven N. Weiss, et al. This instrument is intended in the prior art to fragment a lens nucleus using ultrasonic sound to aid the irrigation/aspiration of the lens.

The prior art use of this instrument to fragment the lens with ultrasonic sound, a procedure called phako emulsification, has several disadvantages, such as: (1) the instrument is larger than desirable and thus may cause damage to the cornea at the site of entry; (2) the prior art use of the instrument imparts so much energy into the eye as to increase the possibility of damage to the structure of the anterior segment; (3) the prior art use of the instrument uses much fluid particularly during the nucleus fragmentation and during the irrigation and aspiration process of the cortex, thus increasing the possibility of damage to the corneal endothelium, sometimes to the extent of reducing the visibility of the surgeon during the operation because of corneal stromal edema and fluid turbulence in the anterior chamber; (4) the instrument increases the amount of agitation within the eye from the force of the ultrasonic vibration, thus increasing the possibility of damage to the eye structure by bombardment with nuclear fragments flying from the point of impact of the instrument with the nucleus; and (5) turbulence of the inflowing fluid can wash away a large number of non-regenerable vital cells of the corneal endothelium.

SUMMARY OF THE INVENTION

Accordingly, it is an object of the invention to provide an improved technique for cataract removal through a small incision.

It is a further object of the invention to provide a novel instrument for fragmenting the lens during cataract removal surgery.

It is a still further object of the invention to provide a novel technique for cataract removal which first delineates the layers of the nucleus, then with low expenditure of energy, shaves the layers of nucleus and cortex and removes the particles by minimal aspiration without irrigation.

It is a still further object of the invention to provide an instrument small enough to fit through a small incision in the capsular bag for breaking up the nucleus.

It is a still further object of the invention to provide an instrument for pulverizing or fragmenting the hardest part of the nucleus of the lens with relatively low expenditure of energy.

It is a still further object of the invention to provide a stand-alone portable instrument for fragmenting the hardest part of a lens.

In accordance with the above and further objects of the invention, a cataract is removed by making a small incision of 2 to 3 millimeters in the sclera along the corneal border at 12 o'clock and another incision of similar dimension in the capsular wall for the insertion of a cannula. A thin cannula is forced to penetrate a few layers of the lens and a small amount of fluid is injected to separate them, a few more layers are penetrated and fluid is injected to separate those and continuing so that a series of circular rings are formed which define loosened layers of nucleus and cortex step-by-step to form the concentric rings.

In those cases where a portion of the nucleus at the center is too hard to penetrate without excessive force that may damage the zonular fibers by displacing the lens, the hardened unpenetrated core of the nucleus is defined by the inner ring and the remainder of the cortex and nucleus are loosened.

After this delineation, the first layer of cortex and nucleus underlying the front or anterior capsule is shaved by moving an instrument, such as a wider bore cannula, through it from the incision to make a series of adjacent gutters extending radially from the incision. When this layer is removed, the underlying layers are removed in the same fashion and so on layer-by-layer. During this process, the last remaining layer may have viscoelastic compound injected under it so that it is lifted and there is less chance of damage to the back wall of the capsular bag.

In the process of making these gutters, thin cylinders of the cortex and nucleus are forced into the lumen of the cannula and removed. Very little, if any, negative pressure may be applied to aspirate but the pressure is prevented from creating negative pressure within the capsular bag especially at the periphery near its annular attachment. Periodically, a smaller cannula may be used to aspirate loose fragments of the cortex during the process. The process is continued until the lens is removed.

To facilitate the penetration of the thin delineating cannula and the progression of the shaving cannula, in one embodiment, a relatively small vibrating and/or rotary motor may be included in the handpiece and connected to produce movement of the cannulas, or of a vibrating wedge or microchisel. In another embodiment, the handpiece can be connected to a console to deliver ultrasonic energy to produce ultrasonic vibration to the cannula or wedge or chisel to enhance their penetrating power or to provide signals to power a rotary motor to increase the shaving ability of a shaving instrument.

This vibrating or rotating movement is useful in cutting through the hardest core of the nucleus and reduce it to narrow strips that can go through the lumen of the shaving cannula easily. The largest portion of the operative tip of the rotary cutter or reciprocating wedge has a diameter of between 18 and 30 gauge.

As can be understood from the above description, the technique and instrument of this invention have several advantages, such as: (1) they only require small incisions for their use; (2) they do not require irrigation which cause turbulence that impairs the visibility of the surgeon and may damage the eye; and (3) they impart relatively small amounts of energy into the eye and thus reduce the turbulence from the energy and the danger of damage to the eye structure.

SUMMARY OF THE DRAWINGS

The above noted and other features of the invention will be better understood from the following detailed description when considered with reference to the accompanying drawings, in which:

FIG. 1 is a block diagram illustrating a surgical technique for removing a cataract in accordance with the invention;

FIG. 2 is a block diagram of one of the steps in the technique of FIG. 1;

FIG. 6 is a fragmentary enlarged view of the tip instrument of FIG. 5;

FIG. 7 is a side elevational view of a portion of the embodiment of FIG. 6 which is the operative point of instrument for fragmenting;

FIG. 8 is a fragmentary sectional side view of a tip portion of FIG. 7;

FIG. 9 is a front elevational view of a portion of FIG. 7;

FIG. 10 is a longitudinal sectional view of another embodiment of instrument for fragmenting a cataract;

FIG. 11 is a schematic circuit diagram illustrating a portion of the embodiment of FIG. 10;

FIG. 12 is a longitudinal sectional view of another embodiment of instrument for fragmenting a cataract;

FIG. 13 is a side elevational view of an operative portion of the instrument of FIG. 12;

FIG. 14 is a fragmentary sectional side view of the tip of the portion of the surgical instrument illustrated in FIG. 13;

FIG. 15 is a front elevational view of the embodiment of FIG. 14;

FIG. 16 is another embodiment of the tip of a tool;

FIG. 17 is a fragmentary sectional side view of the tip of the tool of FIG. 16; and FIG. 18 is a front elevational view of the embodiment of FIG. 17.

DETAILED DESCRIPTION

Figure 3:
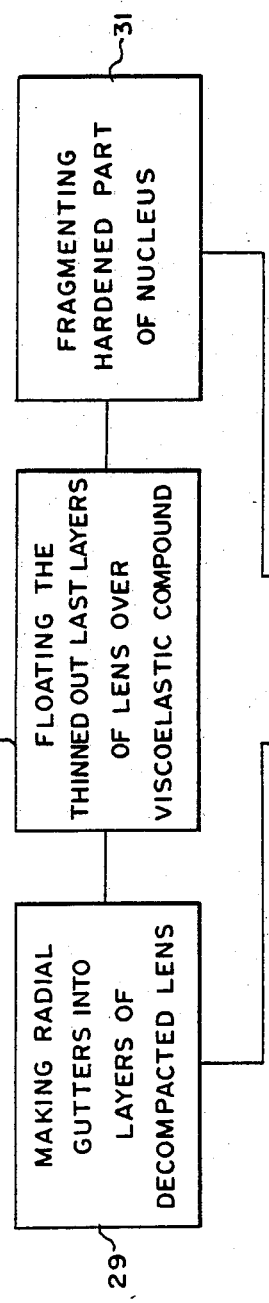
FIG. 3 is a block diagram of another one of the steps in the technique of FIG. 1.

In FIG. 1, there is shown a block diagram generally illustrating the steps in a cataract extraction and lens implantation technique 10 comprising: (1) the step 12 which includes the preliminary substeps of maintaining the anterior chamber and making the incision into the capsular wall; (2) the step 13 of fragmenting and removing the lens; and (3) the step 20 which includes the substeps necessary for implanting the lens.

In performing this technique, the step 12 which includes the substeps required to make the incision and maintain the anterior chamber and the step 20, which includes the substeps necessary for implanting are not by themselves new and many of the steps are described in Anis, Aziz Y. "Illustrated Step-by-Step Description of the Anis Dry Extra Capsular Cataract Extraction Technique With In-the-Bag Lens Implementation"; *Seminars in Opthalmology*, v. 1, N. 2 (Jun.), 1986, pp. 113–129. Moreover, the removal of the lens may not be followed by implantation but may be part of a treatment in which the aphakia is treated by contact lens or glasses.

The step 13 of fragmenting and removing the lens includes: (1) the step 14 of hydrodelineation and decompaction of the lens nucleus; (2) the step 16 of fragmentation or shaving and removal of the decompacted layers of the lens while the lens is fixed in position within the capsular bag; and (3) the step 18 of breaking and removing the hardened part of the nucleus. These steps are all performed through a small incision while the anterior chamber is maintained with a viscoelastic medium.

The step 12 which includes preliminary substeps of maintaining the anterior chamber and making the incision in the capsular bag includes the substep of making an incision in the capsular bag no greater than 3 millimeters in length and preferably in the range of 1 to 2 millimeters. This incision is made while the anterior chamber is maintained and is made as small as possible to maintain the structure of the capsular bag to the extent possible. Through this small incision, the step 13 of fragmenting and removing the lens and the step 20 of implanting a lens are performed.

In FIG. 2, there is shown a block diagram of the step 14 of hydrodelineation and decompaction of the lens nucleus comprising the step 22 of insertion of a cannula through no more than ⅓ of the compacted layers of the lens, the step 24 of decompacting the layers by injection of fluid between the layers of the cortex and nucleus, and the step 26 of repeating the insertion of the cannula and decompacting by injection until as many as possible layers are decompacted with a pressure of insertion low enough to avoid damage to the eye. This amount of pressure should not damage the zonular fibers by displacing the lens.

The insertion of the cannula or other hollow needle is done by hand through only a part of the compacted layers and a fluid is injected in a small amount, such as 1/100 of a milliliter, to lift up the layers. The amount injected is between 1/10 of a milliliter and 1/500 of a milliliter. Because the fluid between layers changes the light path and the index of refraction, a ring appears between the discontinuity separating the layers that are compacted and the layers receiving the fluid. By doing this several times, several concentric rings are shown which separate the compacted center along the optical axis and the raised layers. These concentric circles visibly define the decompacted or loosened part of the lens.

In some eyes, the entire cortex including the nucleus may be decompacted. In other eyes, there is a hardened part of the nucleus of the lens that can not be penetrated by a cannula without risk of damage to other parts of the eye from the pressure. If the size of this hardened part of the nucleus is sufficiently small, it may be aspirated. If it is too large to be aspirated, it may be crushed with a forceps to reduce its size or fragmented with one or more special instruments to be described hereinafter.

The surgeon determines by touch when the hardened compacted part is reached since there is an increased resistance to further penetration. The decompaction by injecting fluid between successive groups of layers of the cortex converts this tactile information to a visible indication useful in fragmenting and removing this hardened part as well as being useful in fragmenting and removing the decompacted part of the lens.

In FIG. 3, there is shown a block diagram illustrating the step 16 of fragmentation and shaving and removal of the decompacted lens while the lens is fixed in position within capsular bag (FIG. 1), comprising the substep 29 of making radial or diverging gutters or furrows into the decompacted layers of the lens, the substep 30 of floating the thinned out last layer of cortex and nucleus, the substep 31 of fragmenting the hardened part of the nucleus and the substep 32 of removing the fragments of the lens. The lens is gradually fragmented and removed as particles no larger than 4 millimeters in diameter and generally between 1 and 2 millimeters in a series of steps while being observed by the surgeon.

The observation of the operation is facilitated because fluid is seldom introduced and the aspiration directly from the capsular bag is rare. The introduction of fluid and aspiration of material directly from the capsular bag instead of only from the cannula causes changes in the location of the capsular wall and the lens fragments and causes turbulence that interferes with the image of the operation. Such interference is reduced to a minimum in the preferred procedure.

Aspiration directly from the capsular bag is reduced to a minimum by the step 32 of removing fragments because the fragments are forced into the open end of the cannula by the pressure of cutting radial gutters or furrows in the cortex and nucleus. Occasionally, the material may be aspirated from the cannula if desired. A special configuration of cannula may be used having lateral openings near the open end that avoid aspiration causing negative pressure from the open end of the cannula.

To reduce the size of the hardened part of the nucleus, if any, the step 31 of fragmenting the hardened part of the nucleus includes the steps of visualizing the hardened part of the nucleus as the inner ring formed during hydrodecompaction and breaking it up with a vibrator or rotating cutter or scraper having a relatively small cannula of 30 gauge or less while it is still held in place within the capsular sac. The vibrator may include an ultrasonic vibrator or a vibrator that moves linearly at a relatively low reciprocating rate, well below the ultrasonic frequency, or instead of a vibrator, the instrument may rotate a cutting edge, or any other mechanism may be used to break, fragment or abrade the lens so that in a series of steps the nucleus is broken down. Also, instead of a hollow cannula with a cutting edge a solid vibrating solid wedge or microchisel can be used. This can vibrate linearly ultrasonically or mechanically at subsonic, frequency.

To reduce the risk of damage to the bottom (posterior for a reclining patient during the operation) wall of the capsular bag, viscous fluid such as a viscoelastic compound may be periodically introduced to float the cortex and provide clearance between the membrane of the capsular sac and the cannula. As the sac is cleared of cortex, the bottom wall becomes visible to the surgeon.

The process of FIGS. 1–3 may be performed with a number of individual instruments. The injection of fluid may be done with a hand-held or automatic syringe or any other suitable device for injecting saline solution or a viscoelastic medium. Similarly, the cutting of divergent grooves in the cortex and nucleus after decompaction and the fragmentation of the hardened part of the nucleus may be done with existing cannula and existing ultrasonic transducer probes utilizing a very small tip, such as tips between 18 and 30 gauge but preferably 20 gauge. However, solid wedge-shaped points ultrasonically driven or tubular rotating cutters or reciprocating cutters at rates of reciprocation and rotating below the ultrasonic frequency range may be used instead to reduce the power input.

Figure 4:
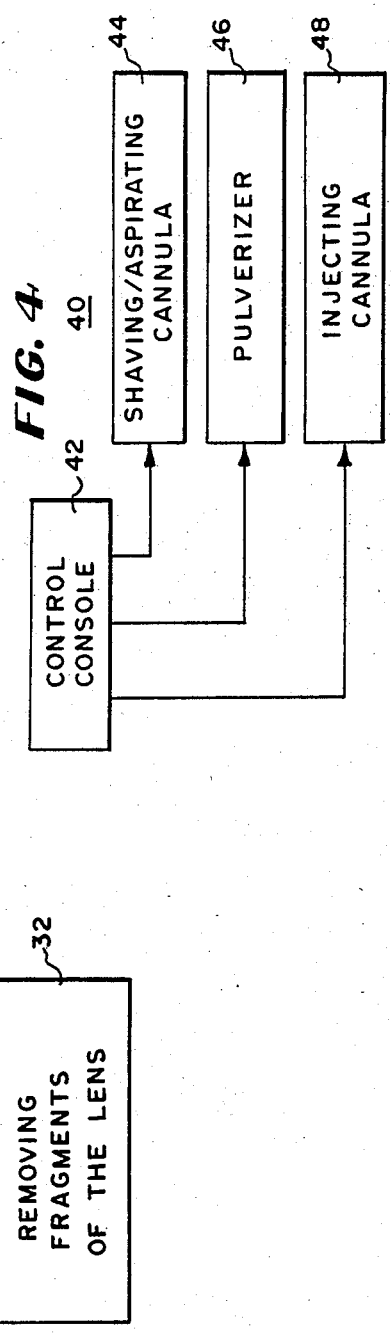
FIG. 4 is a block diagram of one embodiment of the invention.

In FIG. 4, there is shown an integrated instrument 40 having a control console 42, an aspirating cannula 44, a fragmenter handpiece 46, an injecting cannula 48. The control console 42 has setable parameters and readouts and provides inter alia: (1) a vacuum to an aspirating cannula 44 under the control of the operator; (2) ultrasonic electrical signals to a fragmenter handpiece 46 for enabling the shaving/pulverization of the cortex and nucleus of the lens; and (3) in some embodiments, presetable control for the injecting cannula 48 to inject small amounts of fluid between the layers of the cortex and nucleus.

A control console 42 for supplying ultrasonic signals to a fragmenter handpiece 46 or vacuum for an aspirating cannula 44 is known in the art. For example, one such unit is sold by Coopervision, 17701 Cowen, Irvine, Calif., under the brand name Phaco-Emulsifier and described in U.S. Pat. No. 3,693,613 to Kelman, U.S. Pat. No. 3,589,363 to Banko, et al., and U.S. Pat. No. 3,902,495 to Weiss. Similarly, a programmable device suitable for controlling a syringe may be used to control the injecting cannula 48 as described in U.S. Pat. No. 4,475,666 to Bilbrey, et al. The injecting cannula 48 may be of any type having a suitably small tip for penetrating layers of the cortex and nucleus but may also include vibrating tips for better penetration as described hereinafter with respect to the fragmenter handpiece 46.

Figure 5:
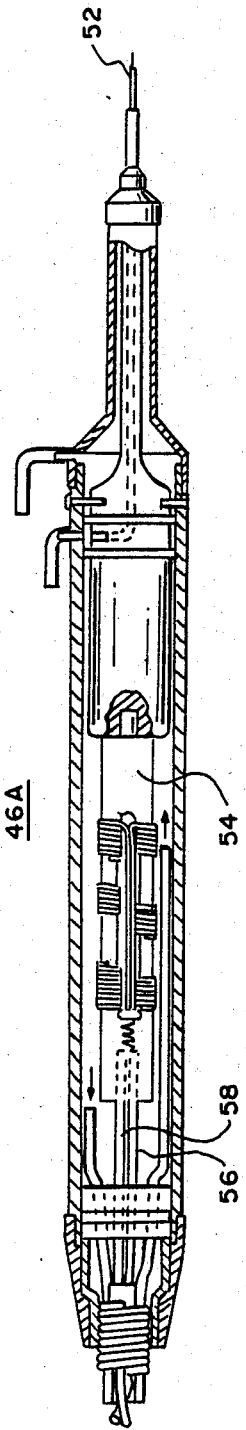
FIG. 5 is a longitudinal sectional view of an instrument used to fragment a cataract in accordance with an embodiment of the invention.

In FIG. 5, there is shown one embodiment 46A of a handpiece, which may serve as a shearing aspirating cannula 44 (FIG. 4) or a fragmenter cannula 46 (FIG. 4). This handpiece is substantially the same as that disclosed in the aforementioned U.S. Pat. Nos. 3,589,363 and 3,693,613. However, it has a smaller tip and operates with reduced power. The use of lower power is consistent with the delineation of the decompacted nucleus of the lens and the process of slowly fragmenting the nuclear layers while it remains fixed in position 16. Generally, the amount of power is less than one-tenth of the power used without the delineation of the nucleus and should be at least less than half of the power used without the steps of first delineating the nuclear layers. The total energy required is also reduced but the most important aspect is the reduction of power and the attendant heat, wear and loss of visibility to the surgeon that is caused by excessive power.

In one embodiment using an ultrasonic handpiece that is substantially identical to that described in the above United States patents, the ultrasonic tip is smaller in size, being within the range of 18 to 30 gauge, and may include lateral openings in its tip. This type of handpiece is shown in FIG. 5 and includes a tip 52, an electrically driven ultrasonic transducer 54, means for electrically connecting the ultrasonic transducer 54 to an outside source of high frequency signals through conductors 56 and 58 and other conduits not of significance herein.

These other conduits are for cooling liquid, treating liquid and venting. They are not so essential when the handpiece is used according to the invention because of the lower power requirements of the invention as compared to the original use for which the fragmenter or shearing/aspirating cannula 44A is designed. It was designed to accommodate relatively high power applications and to be able to introduce substantial volumes of irrigating fluids.

In the embodiment of the cannula 46A, the ultrasonic transducer 54 is a piezoelectric transducer or magnetostrictive transducer which generates vibrations and transmits them through a matching acoustic transformer to the tip. In another embodiment, the same configuration may be used but the frequencies may be lower so that vibrations below the ultrasonic range are transmitted to the tip and provide reciprocating fragmenting action against the fixed cortex of the lens at low power.

The handpiece 46A may also be used as a fragmenter handpiece 46 (FIG. 4) to fragment the hardened nucleus where necessary although other embodiments having a chissel-shaped tip are preferable. When used to fragment the hardened part of the nucleus, it need not aspirate since an aspirating tip may be used instead.

In FIG. 6, there is shown an enlarged view of the tip 52 as it is mounted to the cannula 46A for reciprocating action, illustrating that it may be insertable to fit at the base 60 of the fragmenter or shearing/aspirating cannula 46A at which location it receives reciprocal linear vibrating forces in the ultrasonic range or in a much lower cutting range. To permit aspirating from the cannula without introducing negative pressure in the capsular sac, one or more lateral holes 53 are provided at least 0.25 millimeter but need not be more than 25 millimeters from the end of the tip 52.

In FIG. 7, there is shown an enlarged view of the tip 52 having a pointed end 62 with an open channel 64 through it and a base 66 for attachment to the shear/aspirating or fragmenter cannula 46A. The tip 52 is shown in a sectional view in FIG. 8 and in a front elevational view in FIG. 9 showing the open channel 64 which may be used to apply fluid during fragmentation of the nucleus.

In FIG. 10, there is shown another embodiment of fragmenter handpiece 46B which is self-contained and includes a battery 74 (FIG. 11), a DC/AC inverter 70, and a switch 72. This embodiment is intended to be portable instead of requiring electrical connection to an external source of AC power, as in the embodiment of fragmenter or shearing/aspirating cannula 46A. In this embodiment, the AC signal formed by the DC/AC inverter 70 when power is applied to it from the battery 74 (FIG. 11) by activating the switch 72, energizes the coils 76 to cause the magnetostrictive element 54 to vibrate and thus transmit linear back and forth vibrations to the tip 52A. The DC/AC inverter 70 may be of any selected frequency either in the ultrasound range or in the sonic range but preferably is in the sonic range to maintain a low power density in the capsular sac.

In FIG. 11, there is shown a schematic circuit diagram illustrating a difference between the embodiment of FIG. 10 and the embodiment of FIGS. 5-9. This difference is that a DC battery 74 is connectable to a standard DC/AC inverter 70 through a switch 72 (FIG. 10) to energize the circuit. Because the vibrations are applied directly to the nucleus, the frequency may be lower and with this lowered frequency, there is less energy conversion to heat.

In FIG. 12, there is shown another embodiment of handpiece 44C which may serve as either a fragmenter handpiece or a shear/aspirating cannula. It is self-contained and includes DC batteries 74A and 74C connected in series in a circuit similar to that of the circuit of FIG. 11 except that instead of a DC/AC inverter 70, a DC rotary electric motor 80 is connected to be energized upon the closing of the switch 72C. The DC/AC inverter 70 (FIGS. 10 and 11) is mounted by the hub 60 to a cutter 52B to be described hereinafter so that the cutter 52B rotates. This cutter may be inserted into the cortex and nucleus of the lens and by its rotary motion, fragments the lens with a shearing action moving along the side of the nucleus.

In FIG. 13, there is shown another embodiment of tip 52B mountable by the same screw connector 60 to be moved by the fragmenter but including a wedge-shaped point 90 and being solid and thinner than the embodiment 52 of tip. The spindle and edge may have a diameter of approximately 25 to 30 gauge and is not tubular but solid.

As best shown in FIGS. 14 and 15, the wedge-shaped point 90 includes an edge 92 forming a wedge-shaped member which during reciprocating motion may chop or shear off portions of the nucleus as it is vibrated in the direction of its longitudinal axis with either ultrasonic or sonic level motion.

In FIG. 16, there is shown still another embodiment of tip 52B especially suitable for use with the shear/aspirating cannula 46C and including at its cutting tip 100, a plurality of cutting edges. This tip 100 is intended to be rotated and when moved into intimate contact with the nucleus or cortex, it grinds away portions of the cortex to fragment it with low energy usage. The tip 52B may be of the same diameter and length as tip 52A (FIG. 10), thus being solid and thinner than the embodiment of tip 52 (FIG. 6 and 7).

As best shown in FIGS. 17 and 18, the cutting tip 100 includes a series of sharpened edges 102 which are rotated in a counterclockwise direction, as shown in FIG. 18, to grind away the nucleus and cortex in a relatively slow manner with a minimum of disruption.

In use after the preparatory step related to obtaining access to the capsular bag and maintaining the anterior chamber, an incision is made in the wall of the capsulary sac within the range of 2 or 3 millimeters. The tip of a cannula is thrust through the incision in the wall of the capsular bag and into the lens therein. The layers of cortex and nucleus of the lens are hydrodelineated and decompacted by injecting fluid with an injecting cannula 48 (FIG. 4) between layers in succession to form visible rings localizing sections of decompacted and undecompacted layers of the nucleus of the lens.

When the cortex and nucleus of the lens has been decompacted and marked by hydrolineation, a fragmenter handpiece 46 (FIG. 4) is inserted against the cortex and nucleus and used to cut separating gutters diverging from the incision to form a plurality of cylinder-shaped fragments of decompacted cortex layers.

In using one embodiment of shear/aspirating and fragmenter cannula 44A (FIG. 5), the cutting of the cylinder-shaped sections is aided with ultrasonic vibrations applied to a tip 52 which is between 19 and 30 gauge. In another embodiment, a lower frequency in the sonic or subsonic range is applied by a fragmenter handpiece, such as 44A and 46B. In still another embodiment, the shear/aspirating cannula 46C is used which includes a rotary cutter 52B that gradually grinds away the cortex and nucleus using a low level of power.

In some embodiments, a conical cannula is used to fragment the nucleus but in other embodiments, a rotary grinder may be used to minimize the disturbance within the eye.

If there is a portion of the nucleus that is too large to aspirate and too hard to decompact by inserting fluid with low pressure, it may be crushed or fragmented by a thin wedge-shaped instrument or ground away with a rotary cutter. The entire process of cataract removal is done without irrigating fluids in the preferred embodiment and at most, 1 to 2 milliliters of fluid are used. Thus, there is relatively little damage to the endothelial cells of the cornea or other structures of the eye.

While the capsular sac is relatively intact, a lens implant is inserted through a relatively small opening as described in the above publication of Anis.

As can be understood from the above description, the technique and equipment of this invention has several advantages, such as: (1) there is less damage to the structure of the eye; (2) there is a lower amount of corneal endothelial cells washed away; (3) there is less disruption of the zonular fibers; and (4) a smaller incision is necessary.

Although a preferred embodiment of the invention has been described with some particularity, many modifications and variations are possible in the preferred embodiment without deviating from the invention. Therefore, it is to be understood that within the scope of the appended claims, the invention may be practiced other than as specifically described.

What is claimed is:

1. A method comprising the steps of:
    inserting a cannula through at least one of a plurality of layers of compacted material in the lens of an eye;
    injecting fluid in a volume between 1/500 and 1/10 a milliliter to separate the layers of the lens cortex and lens nucleus;
    repeating the above steps at least two more times, whereby the nucleus and cortex of the lens are decompacted; and
    fragmenting the decompacted layers of the lens.

2. A method in accordance with claim 1 further including the step of:
    aspirating the fragmented decompacted layers of the lens and the hardest portion of the nucleus if the nucleus is smaller than 4 millimeters and if the hardest part of the nucleus is larger than 4 millimeters, fragmenting it into particles smaller than 4 millimeters before aspirating it, whereby the lens is removed with a pressure sufficiently low to avoid damage to the zonular fibers of the eye;
    the step of injecting fluid includes the step of repeatedly injecting fluid between different layers at increasing penetration until a compacted portion of the nucleus is reached which resists the insertion of a needle, whereby a series of visible substantially concentric rings are formed about the hardest portion of the nucleus to aid in visualizing the hardest part of the nucleus.

3. A method according to claim 2 in which the step of fragmenting the lens includes the steps of:
    inserting an elongated tool through an incision into the capsular chamber and against the lens; and
    cutting the lens in a series of paths diverging from the incision to break the lens into a series of wedge-shaped sections.

4. A method in accordance with claim 3 in which the step of cutting the lens includes the step of cutting the lens with a cannula wherein portions of the cortex are forced into the cannula during cutting, whereby large negative pressure is not required to remove the nuclear or cortical portions from the capusular bag.

5. A method in accordance with claim 4 in which the step of cutting the lens with a cannula includes the step of cutting the lens with a cannula having an ultrasonic vibrator mounted within its center, whereby the cutting action is aided.

6. A method in accordance with claim 5 further including the step of fragmenting a hardened portion of the lens nucleus by repeatedly impacting it with a chissel-like point at a high frequency.

7. A method according to claim 5 further including the step of fragmenting a hardened portion of the lens by rotating a grinder against the lens.

8. A method according to claim 7 in which the step of fragmenting the lens includes the step of fragmenting the cortex of the lens into particles having a diameter no larger than 4 millimeters.

9. A method according to claim 2 in which the step of fragmenting the lens includes the step of shearing the lens.

10. A method according to claim 1 in which the step of fragmenting the lens includes the step of shearing a portion of the lens.

* * * * *